US012758338B2

(12) United States Patent
Shademan et al.

(10) Patent No.: US 12,758,338 B2
(45) Date of Patent: Oct. 13, 2026

(54) SYSTEMS AND METHODS FOR OPTIMIZING CONFIGURATIONS OF A COMPUTER-ASSISTED SURGICAL SYSTEM FOR REACHABILITY OF TARGET OBJECTS

(71) Applicant: Intuitive Surgical Operations, Inc., Sunnyvale, CA (US)

(72) Inventors: Azad Shademan, Campbell, CA (US); Mahdi Azizian, San Jose, CA (US); Wen Pei Liu, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 434 days.

(21) Appl. No.: 17/912,791

(22) PCT Filed: Mar. 19, 2021

(86) PCT No.: PCT/US2021/023309

§ 371 (c)(1),
(2) Date: Sep. 19, 2022

(87) PCT Pub. No.: WO2021/194903

PCT Pub. Date: Sep. 30, 2021

(65) Prior Publication Data

US 2023/0139425 A1 May 4, 2023

Related U.S. Application Data

(60) Provisional application No. 62/993,568, filed on Mar. 23, 2020.

(51) Int. Cl.

| | |
|---|---|
| ***A61B 34/37*** | (2016.01) |
| ***A61B 34/00*** | (2016.01) |
| ***A61B 90/00*** | (2016.01) |

(52) U.S. Cl.
CPC .............. *A61B 34/37* (2016.02); *A61B 34/74* (2016.02); *A61B 90/37* (2016.02)

(58) Field of Classification Search
CPC ......... A61B 34/37; A61B 34/74; A61B 90/37; A61B 2034/2046; A61B 2034/2055; A61B 34/30
See application file for complete search history.

(56) References Cited

U.S. PATENT DOCUMENTS

| | | | | |
|---|---|---|---|---|
| 9,439,733 B2 * | 9/2016 | Ha | ......................... | A61B 34/30 |
| 2014/0303643 A1 * | 10/2014 | Ha | ......................... | A61B 34/37 606/130 |

(Continued)

FOREIGN PATENT DOCUMENTS

| | | |
|---|---|---|
| CN | 107811710 A | 3/2018 |
| CN | 108778179 A | 11/2018 |

(Continued)

OTHER PUBLICATIONS

D. Zhang, J. Liu, A. Gao and G. -Z. Yang, "An Ergonomic Shared Workspace Analysis Framework for the Optimal Placement of a Compact Master Control Console," in IEEE Robotics and Automation Letters, vol. 5, No. 2, pp. 2995-3002, Apr. 2020, doi: 10.1109/LRA.2020.2974428. (Year: 2020).*

(Continued)

*Primary Examiner* — Khoi H Tran
*Assistant Examiner* — Trang Dang

(57) ABSTRACT

A configuration optimization system determines a reachability of a target object in a surgical space by a robotic instrument of a computer-assisted surgical system for a first configuration of the computer-assisted surgical system. The configuration optimization system determines a second configuration of the computer-assisted surgical system that improves the reachability of the target object by the robotic instrument. The configuration optimization system provides, (Continued)

to the computer-assisted surgical system, data indicating the second configuration.

13 Claims, 10 Drawing Sheets

(56) References Cited

U.S. PATENT DOCUMENTS

| | | | | |
|---|---|---|---|---|
| 2016/0314710 | A1* | 10/2016 | Jarc | G09B 23/285 |
| 2019/0069962 | A1* | 3/2019 | Tabandeh | A61B 90/39 |
| 2019/0231460 | A1* | 8/2019 | DiMaio | A61B 46/00 |
| 2019/0321117 | A1* | 10/2019 | Itkowitz | A61B 1/0016 |
| 2020/0229879 | A1* | 7/2020 | Magaraggia | A61B 34/30 |
| 2020/0330174 | A1* | 10/2020 | Bertram | A61B 1/000096 |
| 2021/0038335 | A1* | 2/2021 | Maret | A61B 34/74 |
| 2021/0121232 | A1* | 4/2021 | Fuerst | G16H 20/40 |
| 2022/0096164 | A1* | 3/2022 | Jarc | A61B 34/20 |

FOREIGN PATENT DOCUMENTS

| | | | |
|---|---|---|---|
| CN | 109152615 | A | 1/2019 |
| CN | 109275333 | A | 1/2019 |
| WO | WO-2015142953 | A1 | 9/2015 |
| WO | WO-2017147596 | A1 | 8/2017 |
| WO | WO-2017214243 | A1 | 12/2017 |
| WO | WO-2019089226 | A2 | 5/2019 |
| WO | WO-2020167678 | A1 | 8/2020 |

OTHER PUBLICATIONS

International Search Report and Written Opinion for Application No. PCT/US2021/023309, mailed on Aug. 4, 2021, 13 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

International Preliminary Report on Patentability for Application No. PCT/US2021/023309, mailed Oct. 6, 2022, 10 pages.

* cited by examiner

SYSTEMS AND METHODS FOR OPTIMIZING CONFIGURATIONS OF A COMPUTER-ASSISTED SURGICAL SYSTEM FOR REACHABILITY OF TARGET OBJECTS

RELATED APPLICATIONS

The present application is a U.S. National Stage Application under 35 U.S.C. § 371 of International Application No. PCT/US2021/023309, filed on Mar. 19, 2021, which claims priority to U.S. Provisional Patent Application No. 62/993,568, filed Mar. 23, 2020, the contents of which are hereby incorporated by reference in their entirety.

BACKGROUND INFORMATION

Various technologies including computing technologies, robotic technologies, medical technologies, and extended reality technologies (e.g., augmented reality technologies, virtual reality technologies, etc.) have made it possible for users such as surgeons to perform, and be trained to perform, various types of medical operations and procedures. For example, users may perform and be trained to perform minimally-invasive medical procedures such as computer-assisted surgical procedures in clinical settings (e.g., procedures on bodies of live human or animal patients), in non-clinical settings (e.g., procedures on bodies of human or animal cadavers, bodies of tissue removed from human or animal anatomies, etc.), in training settings (e.g., procedures on bodies of physical anatomical training models, bodies of virtual anatomy models in extended reality environments, etc.), and so forth.

During a procedure in any such setting, a user may view imagery of a surgical space associated with a body (e.g., an area internal to the body) as the user directs instruments of a computer-assisted surgical system to perform the procedure with respect to the body at the surgical space. The imagery may be provided by an imaging device included within or attached to the computer-assisted surgical system, such as an endoscope. As various procedures are performed in this way, configurations of the computer-assisted surgical system may affect how efficiently and/or effectively the user is able to perform the procedures.

SUMMARY

The following description presents a simplified summary of one or more aspects of the systems and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An exemplary system includes a memory storing instructions and a processor communicatively coupled to the memory and configured to execute the instructions to determine a reachability of a target object in a surgical space by a robotic instrument of a computer-assisted surgical system for a first configuration of the computer-assisted surgical system; determine a second configuration of the computer-assisted surgical system that improves the reachability of the target object by the robotic instrument; and provide, to the computer-assisted surgical system, data indicating the second configuration.

An exemplary method includes a processor (e.g., a processor of a configuration optimization system) determining a reachability of a target object in a surgical space by a robotic instrument of a computer-assisted surgical system for a first configuration of the computer-assisted surgical system; determining a second configuration of the computer-assisted surgical system that improves the reachability of the target object by the robotic instrument; and providing to the computer-assisted surgical system, data indicating the second configuration.

An exemplary computer-readable medium includes instructions that, when executed by a processor, cause the processor to determine a reachability of a target object in a surgical space by a robotic instrument of a computer-assisted surgical system for a first configuration of the computer-assisted surgical system; determine a second configuration of the computer-assisted surgical system that improves the reachability of the target object by the robotic instrument; and provide, to the computer-assisted surgical system, data indicating the second configuration.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
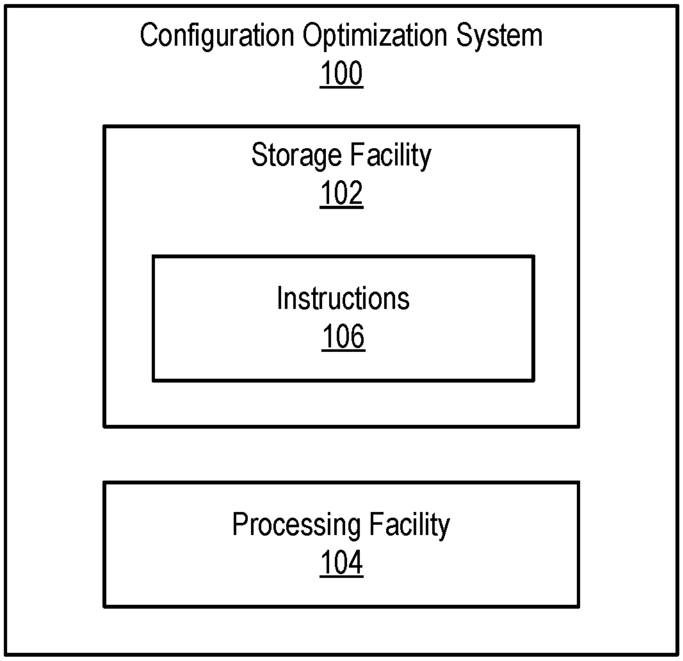
FIG. 1 illustrates an exemplary configuration optimization system according to principles described herein.

Systems and methods for optimizing configurations of a computer-assisted surgical system for reachability of target objects are described herein. During a computer-assisted surgical procedure, a user (e.g., a surgeon) may use (e.g., teleoperate) surgical instruments to interact with various target objects. Such target objects may include any suitable objects in a surgical space, such as anatomical objects, robotic instruments, non-robotic instruments, etc. To interact with target objects using surgical instruments, the surgical instruments must reach the target objects. Moving surgical instruments to the target object may require multiple steps, such as enabling a clutch mode of the computer-assisted surgical system to reposition master controls of the computer-assisted surgical system if the target object is initially out of reach.

A configuration optimization system may determine configurations in which reachability of target objects is determined and optimized based on various parameters as described herein. Reachability may be defined as the effectiveness and/or efficiency with which an element of a computer-assisted surgical system (for example, and instrument, a manipulator, a setup structure, or an input device) can be moved to a target destination(s). The target destination to which the element of the computer-assisted surgical system is to be moved may be a target object, a target location, a target configuration, or any other desired goal. Reachability therefore may be characterized by any suitable parameters, such as distance (e.g., a distance of travel from point to point), deviation from desired orientation (e.g., a difference between a current and desired orientation of an instrument, end effector, robotic linkage, etc.), efficiency (e.g., a total amount of motion required to arrive at the target destination, an ergonomic efficiency of the manipulation of a user control to arrive at the target destination, an ergonomic efficiency of a user to manipulate a user control to cause movement of a point to another point, a measure of the different types of motion and/or inputs necessary to arrive at the target destination etc.), or other measures as described herein, both independently or in any combination. The determined configurations may include configurations from which target objects are more reachable compared to other configurations (e.g., current configurations). Configurations that provide improved reachability compared to other configurations may be referred to as optimal configurations for reachability of target objects. The configuration optimization system may further provide data indicating one or more proposed configurations, such as suggesting alternative configurations to the user and/or automatically implementing improved or optimized configurations to facilitate efficient and/or effective interaction with target objects.

Systems and methods described herein may advantageously increase efficiency and/or effectiveness of surgical instruments reaching target objects in a surgical space. In certain examples, systems and methods may provide guidance for an interaction of a surgical instrument with a target object during a medical procedure. Such guidance may facilitate automatic implementations of configurations in which reachability of the target object is optimized. Moreover, systems and methods described herein may minimize an amount of time required to reach target objects and/or determine configurations in which reachability of target objects is optimized, which may be beneficial to a patient and/or to a surgical team involved in interacting with target objects. These and other advantages and benefits of systems and methods described herein will be made apparent herein.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary configuration optimization system 100 ("system 100") for optimizing configurations of a computer-assisted surgical system for reachability of target objects. System 100 may be included in, implemented by, or connected to one or more components of a computer-assisted surgical system such as an exemplary computer-assisted surgical system that will be described below in relation to FIG. 9. For example, system 100 may be implemented by one or more components of a computer-assisted surgical system such as a manipulating system, a user control system, or an auxiliary system. As another example, system 100 may be implemented by a stand-alone computing system communicatively coupled to a computer-assisted surgical system.

As shown in FIG. 1, system 100 may include, without limitation, a storage facility 102 and a processing facility 104 selectively and communicatively coupled to one another. Facilities 102 and 104 may each include or be implemented by one or more physical computing devices including hardware and/or software components such as processors, memories, storage drives, communication interfaces, instructions stored in memory for execution by the processors, and so forth. Although facilities 102 and 104 are shown to be separate facilities in FIG. 1, facilities 102 and 104 may be combined into fewer facilities, such as into a single facility, or divided into more facilities as may serve a particular implementation. In some examples, each of facilities 102 and 104 may be distributed between multiple devices and/or multiple locations as may serve a particular implementation.

Storage facility 102 may maintain (e.g., store) executable data used by processing facility 104 to perform any of the functionality described herein. For example, storage facility 102 may store instructions 106 that may be executed by processing facility 104 to perform one or more of the operations described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various operations associated with optimizing configurations of a computer-assisted surgical system for reachability of target objects. For example, processing facility 104 may be configured to determine a reachability of a target object in a surgical space by a robotic instrument of the computer-assisted surgical system for a first configuration of the computer-assisted surgical system. Processing facility 104 may further determine (e.g., based on the determination of the reachability of the target object for the first configuration of the computer-assisted surgical system) a second configuration of the computer-assisted surgical system that improves the reachability of the target object by the robotic instrument (e.g., the target object is more reachable in the second configuration than in the first configuration). Processing facility 104 may further provide, to the computer-assisted surgical system, data indicating the second configuration.

These and other operations that may be performed by system 100 (e.g., by processing facility 104 of system 100) are described herein. In the description that follows, any references to functions performed by system 100 may be understood to be performed by processing facility 104 based on instructions 106 stored in storage facility 102.

Figure 2:
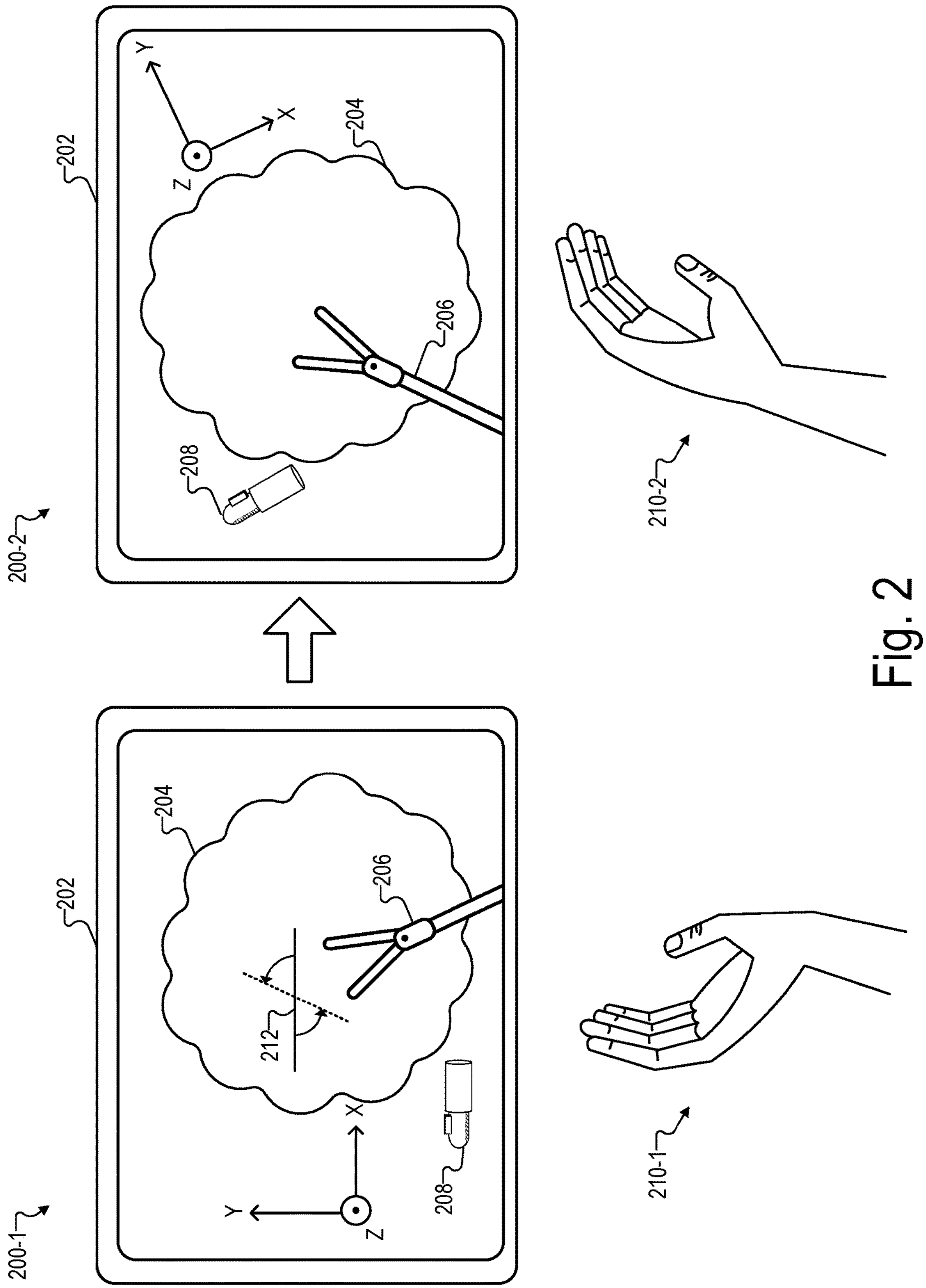
FIG. 2 illustrates a display device displaying imagery from exemplary configurations according to principles described herein.

FIG. 2 illustrates exemplary imagery 200 (e.g., a first image 200-1 and a second image 200-2) of a surgical procedure as displayed by a display device 202 (e.g., a display device of a computer-assisted surgical system). Imagery 200 depicts a surgical space including an anatomical object 204, a surgical instrument 206, and a non-robotic instrument 208. Imagery 200 may be provided by an imaging device (e.g., an imaging device of the computer-assisted surgical system) capturing imagery from a particular viewpoint. For example, image 200-1 shows the surgical space from a first viewpoint while image 200-2 shows the surgical space from a second viewpoint that is different from the first viewpoint. A viewpoint (such as the first and second viewpoints of imagery 200) may refer to a combination of various aspects of position, orientation, configuration, resolution, and the like that together combine to define what imagery the imaging device captures at a particular moment in time. Additional aspects of viewpoints are described further herein. As shown by coordinate axes on each of image 200-1 and image 200-2 (which coordinate axes may or may not actually be shown on display device 202), the viewpoint of image 200-2 is a rotation about a z-axis of the viewpoint of image 200-1.

The surgical space includes anatomical object 204, which may be any anatomical portion of a body of a patient on whom the surgical procedure is being performed. For example, anatomical object 204 may include an internal organ or portions of internal organs, etc.

Surgical instrument 206 may be implemented by any suitable therapeutic instrument (e.g., a tool having tissue-interaction functions), imaging device (e.g., an endoscope), diagnostic instrument, or the like that may be used for a computer-assisted surgical procedure on the patient (e.g., by being at least partially inserted into the patient and manipulated to perform a computer-assisted surgical procedure on the patient). Surgical instrument 206 may also be configured to interact with (e.g., grasp, manipulate, move, image, etc.) target objects such as anatomy (e.g., anatomical object 204) and/or non-robotic instruments (e.g., non-robotic instrument 208) in a surgical space. In some examples, surgical instrument 206 may include force-sensing and/or other sensing capabilities. Surgical instrument 206 may be coupled to a manipulator arm of the computer-assisted surgical system and configured to be manipulated by the manipulator arm as controlled (e.g., teleoperated) by a user (e.g., a surgeon) of the computer-assisted surgical system using a set of master controls of the computer-assisted surgical system.

Non-robotic instrument 208 may be any suitable instrument that is not coupled to a manipulator arm of the computer-assisted surgical system. As shown in imagery 200, an example non-robotic instrument 208 is a sensor (e.g., an ultrasound probe). Other example non-robotic instruments may include any other suitable sensors (e.g., drop-in optical coherence tomography (OCT) sensors, drop-in rapid evaporative ionization mass spectrometry (REIMS) devices, etc.), imaging devices, affixation devices or instruments (e.g., sutures, staples, anchors, suturing devices, etc.), etc.

Non-robotic instrument 208 may be an example of a target object for interaction by the computer-assisted surgical system. Other target objects may include any suitable object found in a surgical space that can be interacted with by surgical instrument 206. Such suitable objects may include anatomical objects, other robotic instruments (e.g., robotic instruments coupled to a system different from the computer-assisted surgical system), other non-robotic instruments, etc.

During a surgical procedure being performed with a computer-assisted surgical system (e.g., performed by a user using the computer-assisted surgical system), a configuration optimization system (e.g., system 100) may identify a target object in a surgical space. For example, system 100 may identify that non-robotic instrument 208 is a target object that the user may want to interact with using surgical instrument 206. System 100 may identify the target object in any suitable manner. For instance, system 100 may use image processing and object recognition algorithms to determine that non-robotic instrument 208 is a non-robotic instrument that is a potential target object. System 100 may be configured to consider any and/or particular non-robotic instruments or types of instruments as a potential target object. Additionally or alternatively, system 100 may receive an indication of a target object from the user.

For the user to use surgical instrument 206 to interact with non-robotic instrument 208, surgical instrument 206 must reach non-robotic instrument 208. To facilitate surgical instrument 206 reaching non-robotic instrument 208 in an efficient and/or effective manner, system 100 may determine a reachability of non-robotic instrument 208 by surgical instrument 206 for a first configuration of the computer-assisted surgical system such as a current configuration of the computer-assisted surgical system. The configuration may include any suitable information and/or parameters relating to a reachability of non-robotic instrument 208 by surgical instrument 206. For example, a configuration may include a pose (e.g., a position and/or an orientation) of non-robotic instrument 208, a pose of surgical instrument 206, a pose of a set of master controls of the computer-assisted surgical system, a viewpoint provided by the imaging device of the computer-assisted surgical system, a target interaction with non-robotic instrument 208, etc.

System 100 may determine a reachability of non-robotic instrument 208 based on the parameters of the current configuration. For instance, image 200-1 shows a first configuration of the computer-assisted surgical system for which system 100 may determine the reachability of non-robotic instrument 208. The reachability may depend on a current position of non-robotic instrument 208 relative to a current position of surgical instrument 206 (e.g., a distance between the current positions of non-robotic instrument 208 and surgical instrument 206). The reachability may further depend on a current orientation of non-robotic instrument 208 relative to a current orientation of surgical instrument 206. For example, orientation of non-robotic instrument 208 may affect a distance surgical instrument 206 is to travel to be able to interact with non-robotic instrument 208. The reachability may further depend on a target interaction with non-robotic instrument 208. For example, the target interaction may affect which part of non-robotic instrument 208 is to be reached, which may also affect the distance to be traveled by surgical instrument 206. The reachability may further depend on a pose of a master control that is manipulated by a user to control movement of surgical instrument 206. For example, orientation of surgical instrument 206 may correspond to an orientation of the set of master controls, which may in turn affect a pose (e.g., pose 210-1 or pose 210-2) of a hand and wrist of a user (e.g., a surgeon). In this example, pose 210-1 may be a relatively difficult pose from which the user is to maneuver the master controls in a direction toward non-robotic instrument 208. Additionally, a position of the master controls may determine how far the master controls may be configured to move in the direction toward non-robotic instrument 208. The reachability may further depend on a viewpoint provided by an imaging device of the computer-assisted surgical system. For example, a visibility of the target object may affect the reachability of the target object. The examples of parameters described above are illustrative. Any suitable additional or alternative parameters may be used by system 100 to determine a reachability of a target object. Examples of determining reachability of a target object are discussed herein.

System 100 may determine (e.g., based on the determined reachability of non-robotic instrument 208 by surgical instrument 206 in the current configuration) a second configuration such as a suggested configuration that improves the reachability of non-robotic instrument 208 by surgical instrument 206 (e.g., the non-robotic instrument 208 may be more reachable in the suggested configuration than in the current configuration). For example, image 200-2 shows a second configuration of the computer-assisted surgical system in which non-robotic instrument 208 is more reachable than in the first configuration shown in image 200-1. Non-robotic instrument 208 may be more reachable in the second configuration at least in part because a pose of surgical instrument 206 has changed to allow the user to change the hand and wrist of the user to pose 210-2. Pose 210-2 may be an easier pose from which to move the master controls in a direction to manipulate surgical instrument 206 toward non-robotic instrument 208 than pose 210-1, given kinematics of a human hand, wrist, and/or arm. Thus, though the distance between surgical instrument 206 and non-robotic instrument 208 may not have changed between the first configuration and the second configuration, a change in orientation of surgical instrument 206 may result in a configuration in which non-robotic instrument 208 is more reachable. Further, such a change in orientation may correspond to a change in viewpoint to allow the user's hand to remain in a corresponding orientation with surgical instrument 206.

System 100 may further provide data indicating the second configuration, such as by displaying the second configuration on display device 202 (as shown in image 200-2). Such a display may depict an actual corresponding change in the configuration of the computer-assisted surgical system. Additionally or alternatively, image 200-2 may be displayed in a manner that indicates a suggestion of a change of the first configuration (e.g., using a different opacity, a different size, with any suitable indicator indicating a different display mode, etc.) that is to be accepted by the user before the actual change in the configuration is implemented. Additionally or alternatively, the data may include other suggestions or guidance (e.g., visual, auditory, haptic, etc.) to implement the second configuration from the first configuration. Additionally or alternatively, the data may include commands that direct the computer-assisted surgical system to automatically change the configuration of the computer-assisted surgical system, such as upon an indication received from the user to implement a configuration (e.g., a user acceptance of suggested new configuration) in which reachability of non-robotic instrument 208 is optimized.

Figure 3:
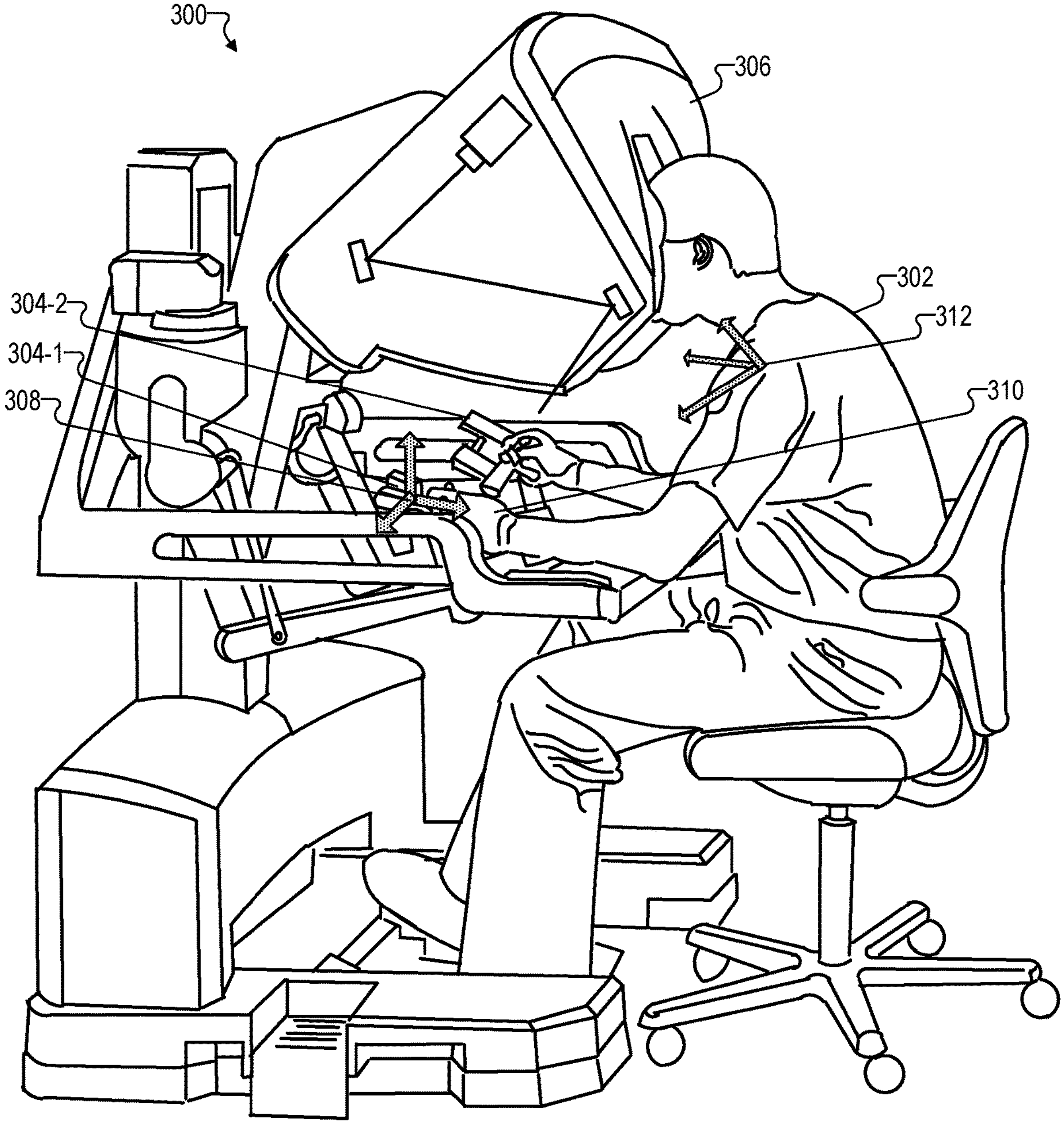
FIG. 3 illustrates an exemplary portion of a computer-assisted surgical system according to principles described herein.

FIG. 3 shows a portion (e.g., a user control system 300) of an exemplary computer-assisted surgical system. A user 302 is shown manipulating a set of master controls 304 (e.g., a left master control 304-1 and a right master control 304-2) and viewing, through a viewer 306, imagery provided by an imaging system (e.g., an imaging device of the computer-assisted surgical system). An example implementation of the computer-assisted surgical system is further described in FIG. 9.

A reachability of a target object may be based on a dexterity (e.g., kinematic dexterity and/or dynamic dexterity) of master controls 304 (e.g., master control 304-1). The dexterity may be based on limits of master control 304-1 imposed by the computer-assisted surgical system. Such limits may be electromechanical (e.g., based on physical construction of the computer-assisted surgical system, location of surrounding equipment, size of room, location of users, etc.), based on the surgical space, based on anatomical objects, etc. A set of coordinate axes 308 represents the dexterity of master control 304-1 from a given pose.

The reachability may be further based on a dexterity of user 302. The dexterity may be based on biomechanical limits of user 302 to move a hand 310 of user 302 to particular poses. The dexterity may be determined based on a model of movement of arms of user 302 (e.g., modeling joints from shoulder to elbow to wrist, etc.). Additionally or alternatively, dexterity may be determined using a camera capturing images of user 302 along with image processing algorithms and/or machine learning algorithms to track movement of user 302, a current position of user 302, a set of possible poses of user 302, a set of preferred poses of user 302, a set of ergonomically advantageous poses of user 302, etc. A set of coordinate axes 312 represents the dexterity of user 302 from a given pose.

Figure 4:
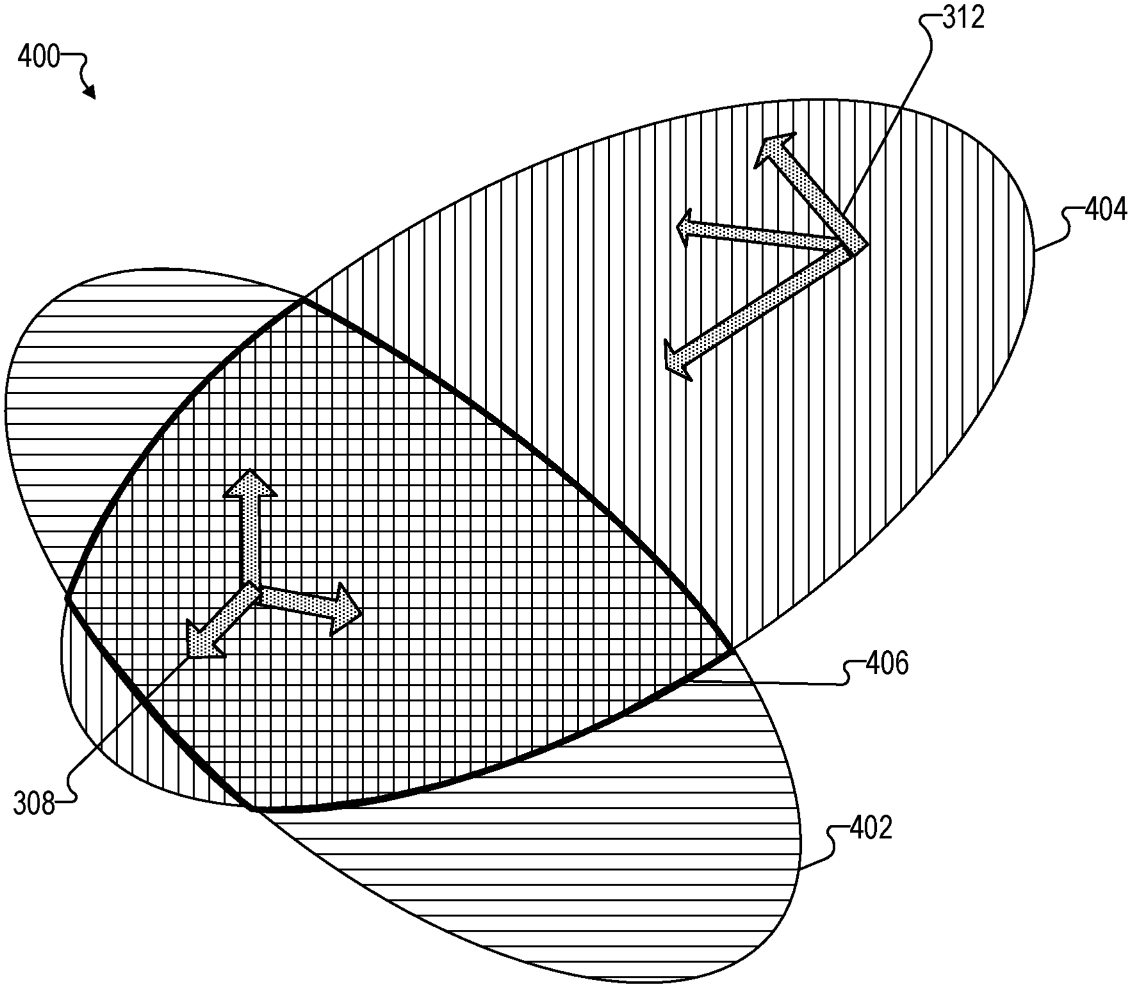
FIG. 4 illustrates exemplary workspaces for optimizing configurations according to principles described herein.

Based at least in part on the dexterity of master controls 304 and the dexterity of user 302, system 100 may determine reachability of a target object. For example, FIG. 4 shows an exemplary model 400 that depicts a workspace 402 of a set of master controls (e.g., master control 304-1) and a workspace 404 of a user (e.g., user 302).

In some examples, workspace 402 may represent an area defining some or all points in which master control 304-1 is configured to be able to move (e.g., within the limits imposed by computer-assisted surgical system 300). Workspace 404 may represent an area defining some or all points in which user 302 is able to maneuver master control 304-1. A reachability of a target object may depend on whether and/or where the target object is located within a joint workspace 406 in which workspace 402 and workspace 404 overlap, as joint workspace 406 may represent the points in space for which master control 304-1 is configured to move and user 302 is able to maneuver master control 304-1. Thus, a configuration that results in the target object being placed more centrally in joint workspace 406 may be considered a configuration in which the target object is more reachable compared to another configuration.

Additionally or alternatively, workspace 402 may represent an area defining points in which master control 304-1 is configured to move based on a current pose of master control 304-1. Likewise, workspace 404 may represent an area defining points in which user 302 is able to maneuver master control 304-1 based on a current pose of master control 304-1 (which may correspond to a current pose of a wrist and hand of user 302). Thus, workspace 402 and/or workspace 404 may dynamically change as master control 304-1 is moved. Consequently, joint workspace 406 may also change dynamically in accordance with a change to workspace 402 and/or workspace 404. In such an example, a configuration may be optimized for one (or more) of workspace 402, 404, or 406 to determine a configuration in which reachability of a target object is optimized. For instance, system 100 may define a cost function that would determine a pose of master control 304-1 that optimizes for one or more dynamic properties of workspace 402 and/or master control 304-1. Such dynamic properties may include any suitable properties such as an area of workspace 402, a center of gravity of master control 304-1, an economy of motion of master control 304-1, etc. Additionally or alternatively, the cost function may optimize for one or more dynamic properties of workspace 404 and/or user 302. Such dynamic properties may include any suitable properties such as an area of workspace 404, an ergonomic optimization for user 302, an economy of motion for user 302, etc. Additionally or alternatively, the cost function may optimize for dynamic properties of both workspace 402 and 404 (e.g., one or more dynamic properties of joint workspace 406, master control 304-1, and/or user 302). Thus, placing master control 304-1 in an optimal pose defined by such a cost function may result in a configuration in which reachability of a target object is optimized.

Furthermore, system 100 may optimize configurations for reachability for more than one target object. For example, user 302 may desire to alternate a series of interactions with two target objects, going back and forth. System 100 may optimize for a configuration taking into consideration reachability of both (or any number of) target objects.

As described, a system 100 may optimize a configuration by changing a pose of a set of master controls (e.g., master controls 304). System 100 may place master control 304-1 (and/or master controls 304) in a different pose (e.g., an optimal pose for reachability of the target object) by directing the computer-assisted surgical system to operate in a clutch mode. The clutch mode may decouple master controls 304 from surgical instruments (e.g., surgical instrument 206) so that master controls 304 may be repositioned without a corresponding movement of surgical instruments. In this way, in some examples, system 100 may provide data indicating a proposed configuration by automatically changing a pose of master controls 304 to a more optimal pose that results in an optimized reachability of a target object by the surgical instrument. For instance, if an arm of user 302 were fully extended in a first pose of master control 304-1 and a target object were located farther in a same direction as the extension of the arm, user 302 may be unable to reach the target object. However, if system 100 were to move master control 304-1 in clutch mode so that the arm of user 302 is no longer fully extended while keeping the relative pose of a corresponding surgical instrument to the target object unchanged, user 302 could then easily extended the arm in the same direction to reach the target object. In this instance, a first configuration may include a first pose of master control 304-1 and a first pose of the surgical instrument. The second configuration may include a second pose of master control 304-1 that then corresponds to the first pose of the surgical instrument, as master control 304-1 has moved in clutch mode while the surgical instrument has not.

As mentioned previously, in some instances, a change in a pose of master control 304-1 may result in a change in a viewpoint provided by the computer-assisted surgical system and vice versa. Such corresponding changes may allow user 302 to keep an orientation of a hand and/or wrist of user 302 consistent with an orientation of a corresponding surgical instrument that user 302 sees on a display device.

Figure 5:
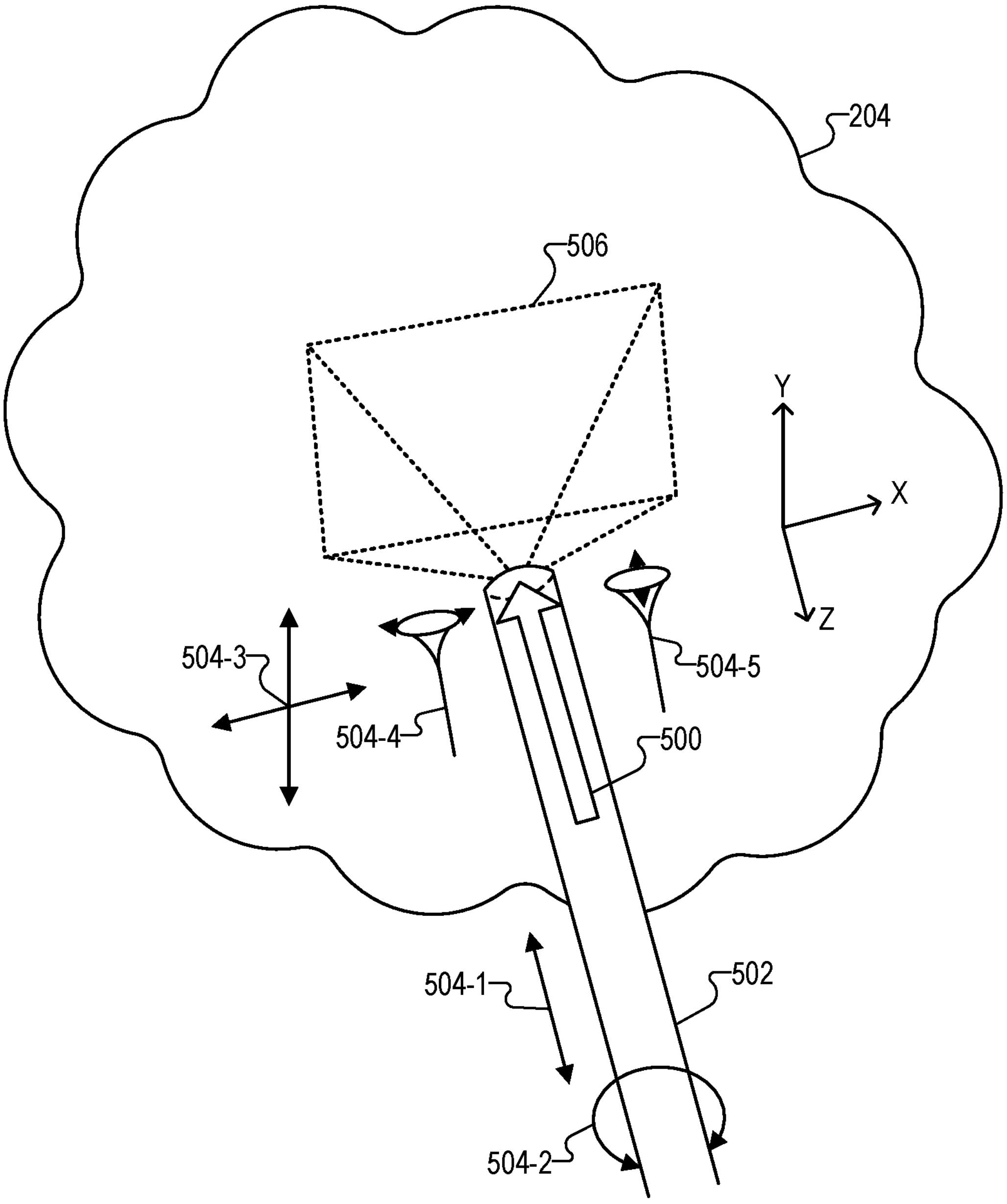
FIG. 5 illustrates an exemplary viewpoint of a configuration from which an imaging device captures imagery according to principles described herein.

For example, FIG. 5 shows an exemplary viewpoint 500 from which an imaging device 502 (e.g., an imaging device of computer-assisted surgical system 300) captures imagery of an anatomical object (e.g., anatomical object 204). FIG. 5 depicts viewpoint 500 as an arrow stretching along the shaft of imaging device 502 to suggest that, as alterations are made to the position, orientation, configuration, resolution, etc. of imaging device 502, viewpoint 500 will be adjusted accordingly.

Viewpoint 500 may be defined by various aspects of position, orientation, configuration, resolution, and so forth of imaging device 502. Each of these aspects will be referred to herein as different aspects of an orientation or as different types of orientations 504 (e.g., orientations 504-1 through 504-5) of viewpoint 500.

As shown, a zoom orientation 504-1 of viewpoint 500 relates to an apparent position of viewpoint 500 along the longitudinal axis of the shaft of imaging device 502. Thus, for example, an adjustment in zoom orientation 504-1 may result in imagery that looks larger (closer) or smaller (farther away) as compared to an initial zoom orientation 504-1 that has not been adjusted. In certain implementations, adjustments to zoom orientation 504-1 may be made by physically moving or sliding imaging device 502 closer to a portion of anatomical object 204 that is being captured or farther from the portion of anatomical object 204 that is being captured. Such zoom adjustments may be referred to herein as optical zoom adjustments. In other implementations, adjustments may be made without physically moving or adjusting the physical orientation of imaging device 502. For example, zoom adjustments may be made optically by internally changing a lens, lens configuration, or other optical aspect of imaging device 502, or by applying a digital zoom manipulation to the image data captured by imaging device 502.

A horizon orientation 504-2 of viewpoint 500 relates to a rotation of imaging device 502 along the longitudinal axis of the shaft of imaging device 502 (i.e., a z-axis according to a coordinate system illustrated in FIG. 5). Thus, for example, an adjustment of 180° in horizon orientation 504-1 would result in imagery that is upside down as compared to a horizon orientation of 0°. In certain implementations, adjustments to horizon orientation 504-1 may be made by physically rotating imaging device 502, while in other implementations, such adjustments may be made without physically moving or adjusting the physical orientation of imaging device 502. For example, horizon adjustments may be made by digitally manipulating or processing the image data captured by imaging device 502.

A planar orientation 504-3 of viewpoint 500 relates to a position of imaging device with respect to a plane of anatomical object 204 that is being captured. As such, planar orientation 504-3 may be adjusted by panning imaging device 502 left, right, up, or down orthogonally to a longitudinal axis (i.e., parallel to an x-y plane according to the coordinate system shown in FIG. 5). When planar orientation 504-3 is adjusted, the imagery of the body scrolls so that a different part of the body is depicted by the image data after the adjustment to planar orientation 504-3 is made than before.

As mentioned above, certain implementations of imaging device 502 may be jointed, flexible, or may otherwise have an ability to articulate to capture imagery in directions away from the longitudinal axis of imaging device 502. Additionally, even if a particular implementation of imaging device 502 is rigid and straight, settings for angled views (e.g., 30° angled views up or down, etc.) may be available to similarly allow imaging device 502 to capture imagery in directions other than straight ahead. Accordingly, for any of these implementations of imaging device 502, a yaw orientation 504-4 that affects a heading of imaging device 502 along a normal axis (i.e., a y-axis of the coordinate system shown), as well as a pitch orientation 504-5 that affects the tilt of the imaging device along a transverse axis (i.e., a x-axis of the coordinate system shown) may also be adjustable.

While various orientations 504 have been explicitly described, it will be understood that various other aspects of how imaging device 502 captures imagery of anatomical object 204 may similarly be included as adjustable aspects of the orientation of imaging device 502 in certain implementations.

Based on viewpoint 500, imaging device 502 is shown to capture a particular field of view 506 of anatomical object 204. It will be understood that field of view 506 may change in various ways (e.g., move side to side, get larger or smaller, etc.) as various orientations 504 of viewpoint 500 of imaging device 502 are adjusted.

Figure 6C:
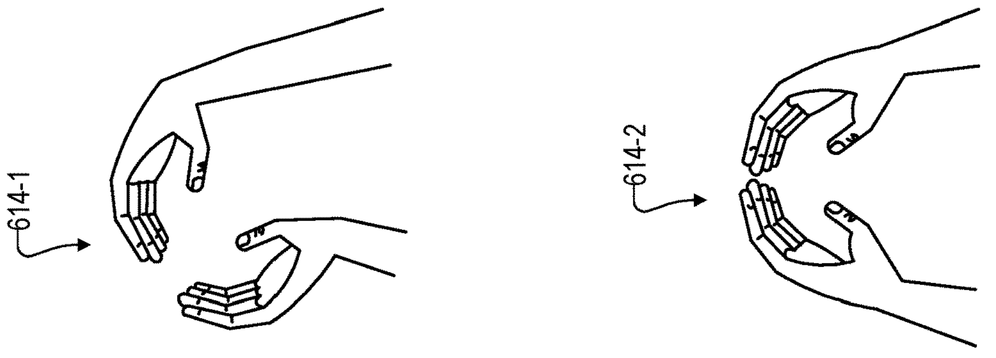
FIG. 6C illustrates exemplary wrist postures used by the user for the different configurations of the computer-assisted surgical system in FIGS. 6A and 6B according to principles described herein.
Figure 6B:
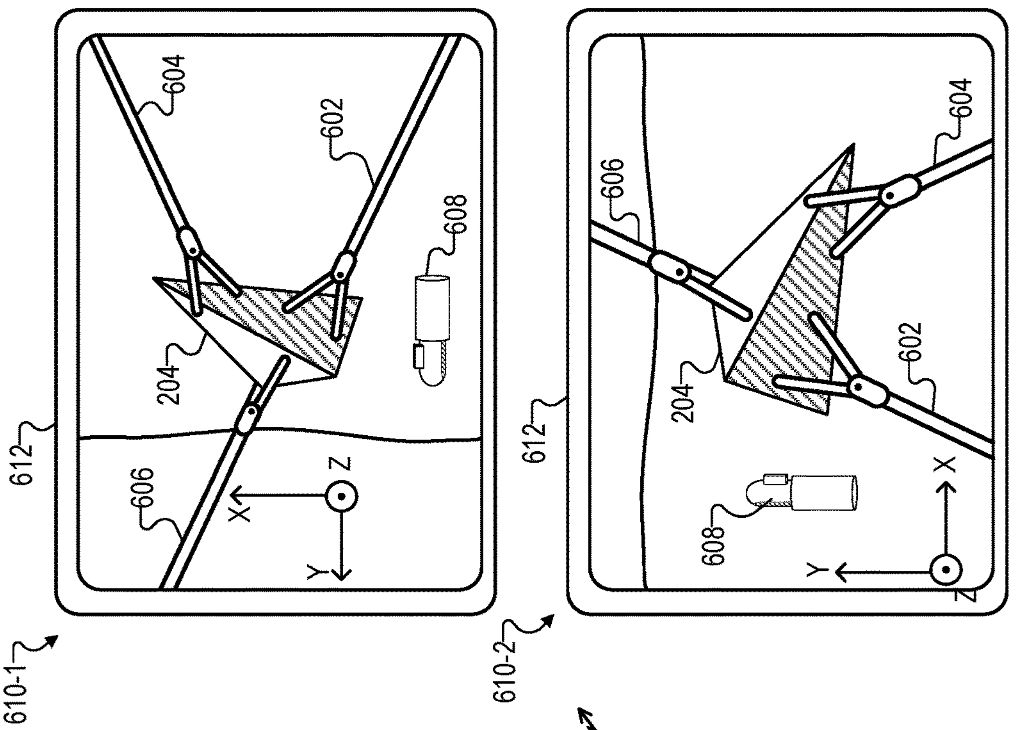
FIG. 6B illustrates an exemplary display device on which the anatomical object in FIG. 6A is displayed in the different configurations of the computer-assisted surgical system according to principles described herein.
Figure 6A:
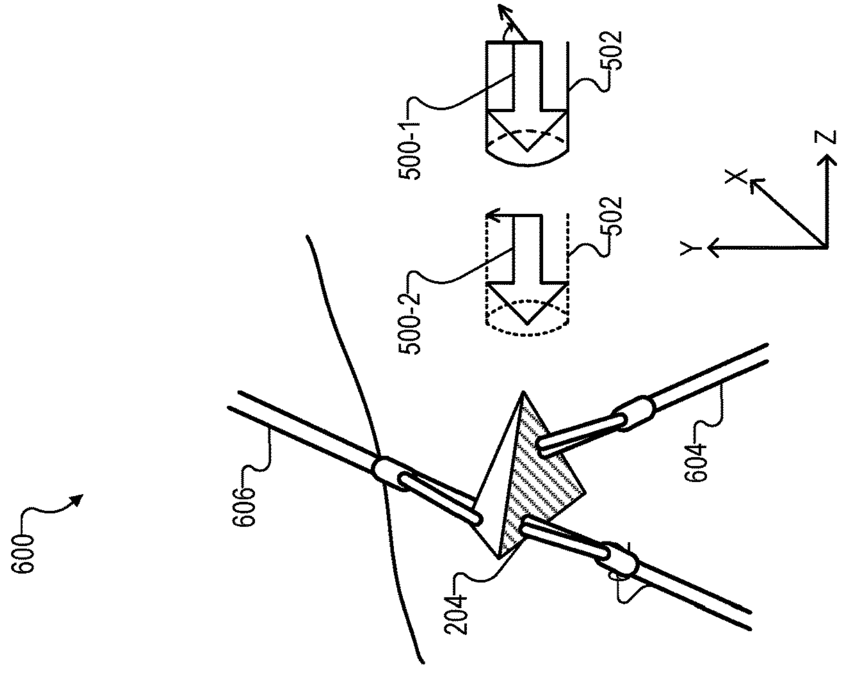
FIG. 6A illustrates an imaging device of a computer-assisted surgical system capturing imagery of an anatomical object during a procedure from exemplary viewpoints of different configurations of the computer-assisted surgical system according to principles described herein.

FIG. 6A shows an exemplary procedure 600 during which a computer-assisted surgical system performs a plurality of operations with respect to an anatomical object (e.g., anatomical object 204), while an imaging device (e.g., imaging device 502, which may be included within the computer-assisted surgical system) captures imagery of anatomical object 204 from different exemplary viewpoints 500 (e.g., viewpoints 500-1 and 500-2). More specifically, FIG. 6A depicts, from a side perspective showing the position of imaging device 502, a specific portion of anatomical object 204 where an incision has been made, and a relative position of a distal end of imaging device 502 with respect to the incision. As shown, various surgical instruments 602, 604, and 606 are being used to perform one or more operations with respect to anatomical object 204 in the surgical space. For example, surgical instruments 602 and 604 may be used primarily to manipulate tissue and/or tools in furtherance of the operations being performed, while surgical instrument 606 may be used to hold certain portions of tissue out of the way or to otherwise facilitate the performance of the operations.

In FIG. 6A, the distal end of imaging device 502 is depicted in a first configuration (depicted using solid lines) and in a second configuration (depicted using dotted lines). As shown, imaging device 502 has a first viewpoint 500-1 in the first configuration and a second viewpoint 500-2 in the second configuration. A small arrow depicted at the back of each of viewpoints 500-1 and 500-2 indicates a horizon orientation (i.e., how imaging device 502 is rotated along the longitudinal axis) for that viewpoint with respect to a three-dimensional ("3D") coordinate system shown to have X, Y, and Z dimensions. More particularly, the horizon orientation of viewpoint 500-1 is shown to have the positive X dimension facing up, while the horizon orientation of viewpoint 500-2 is shown to have the positive Y dimension facing up. Along with viewpoints 500-1 and 500-2 differing in their respective horizon orientations, the zoom orientation from viewpoint 500-1 to 500-2 is also shown to be adjusted because viewpoint 500-2 is nearer to (i.e., optically zoomed in on) the tissue of anatomical object 204.

FIG. 6B illustrates an exemplary display device 612 upon which imagery 610 (e.g., image 610-1 and image 610-2) captured from viewpoints 500-1 and 500-2 during procedure 600 is displayed. Specifically, image 610-1 captured by imaging device 502 from viewpoint 500-1 is displayed on a display device 612 in the first configuration, while image 610-2 captured by imaging device 502 from viewpoint 500-2 is displayed on display device 612 in the second configuration when the viewpoint of imaging device 502 has been adjusted (i.e., zoomed in and rotated 90 degrees). To help clarify what is depicted within images 610-1 and 610-2 and how these are different from one another, the same coordinate system included in FIG. 6A is also shown alongside each of images 610-1 and 610-2 in FIG. 6B. In both cases, the Z-dimension is illustrated by a dot notation to indicate that the z-axis is coming straight out of the imaging device screen (i.e., parallel with the longitudinal axis of imaging device 502 in this example). However, while the X-dimension is illustrated as facing up in image 610-1, the 90° adjustment to the horizon orientation from viewpoint 500-1 to viewpoint 500-2 is shown to result in the Y-dimension facing up in image 610-2. As mentioned above, switching from a first viewpoint to a second viewpoint may result in a second configuration including a more natural, comfortable, and efficient wrist posture in which target object 608 is more reachable than a first configuration.

To illustrate, FIG. 6C shows exemplary wrist postures 614-1 and 614-2 used by a user (e.g., user 302) to perform a procedure while viewing imagery 610 from viewpoints 500-1 and 500-2, respectively. For each of wrist postures 614-1 and 614-2, the left and rights wrists are posed to respectively mimic poses of surgical instruments 602 and 604. Once computer-assisted surgical system 300 is in a normal operating mode (e.g., as opposed to a clutch operating mode), surgical instrument 602 may thus be configured to follow and be directed by the left hand and wrist of the user, while surgical instrument 604 may be configured to follow and be directed by the right hand and wrist of the user (e.g., via a set of master controls of computer-assisted surgical system 300). However, as illustrated by FIG. 6C, the wrist posture required to direct the instruments as they are posed in image 610-1 is significantly different from the wrist posture required to direct the instruments as posed in image 610-2.

Specifically, as shown, wrist posture 614-1, which is associated with the first configuration, including viewpoint 500-1 and with surgical instruments 602 and 604 as posed in image 610-1, may limit reachability in certain directions (such as toward target object 608). Accordingly, system 100 may determine the second configuration, including viewpoint 500-2 and with surgical instruments 602 and 604 as posed in image 610-2, is a configuration in which target object 608 is more reachable than the first configuration.

While FIGS. 6A-6C illustrate a viewpoint adjustment that includes a change to both a horizon orientation and a zoom orientation, it will be understood that system 100 may define the second viewpoint in any suitable manner to optimize reachability of target object 608.

Figure 7:
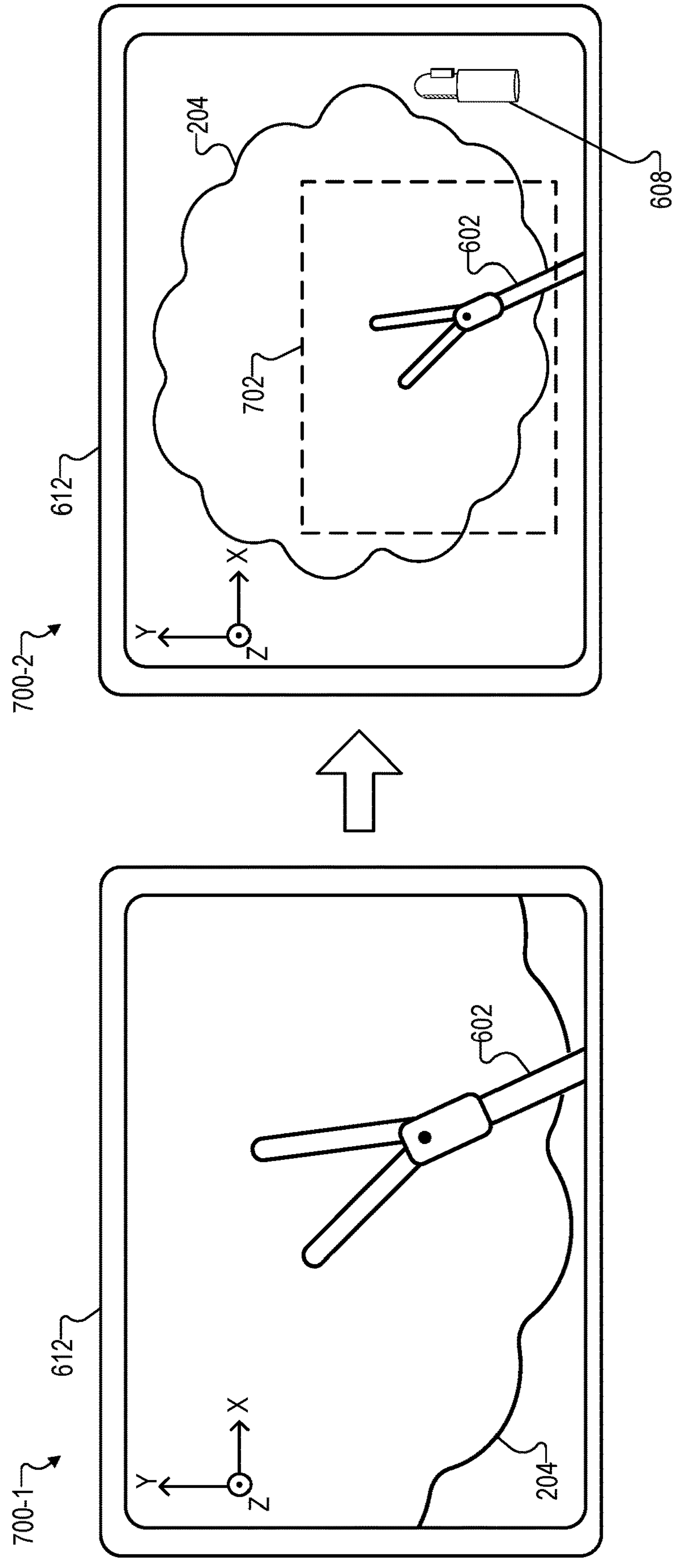
FIG. 7 illustrates exemplary configurations of a computer-assisted surgical system according to principles described herein.

As another example, FIG. 7 illustrates display device 612 displaying image 700-1 from a first viewpoint 702 of a first configuration and, subsequently, displaying image 700-2 from a second viewpoint of a second configuration that has a different zoom orientation than the first viewpoint 702. In this example, system 100 may identify that a target object (e.g., target object 608) is more reachable in the second configuration than the first configuration because it is more visible in the second viewpoint than in the first viewpoint 702. Additionally, the second viewpoint may also correspond to a different scale of movement of a surgical instrument (e.g., surgical instrument 602) with respect to target object 608. Whether the scale of movement (and a corresponding distance for movement of a set of master controls) changes, an increased visibility of target object 608 and/or a path to target object 608 may be considered a configuration in which reachability of target object 608 is optimized. In imagery 700, system 100 may determine that the first viewpoint 702 is too closely zoomed in to provide visibility of target object 608 and, as a result, may determine that a more optimal viewpoint would have a zoom orientation that is zoomed out to provide more visible area. While imagery 700 shows different zoom levels, any suitable changes in viewpoint (e.g., any of the orientations described) may result in configurations with optimized reachability of target object 608.

Figure 8:
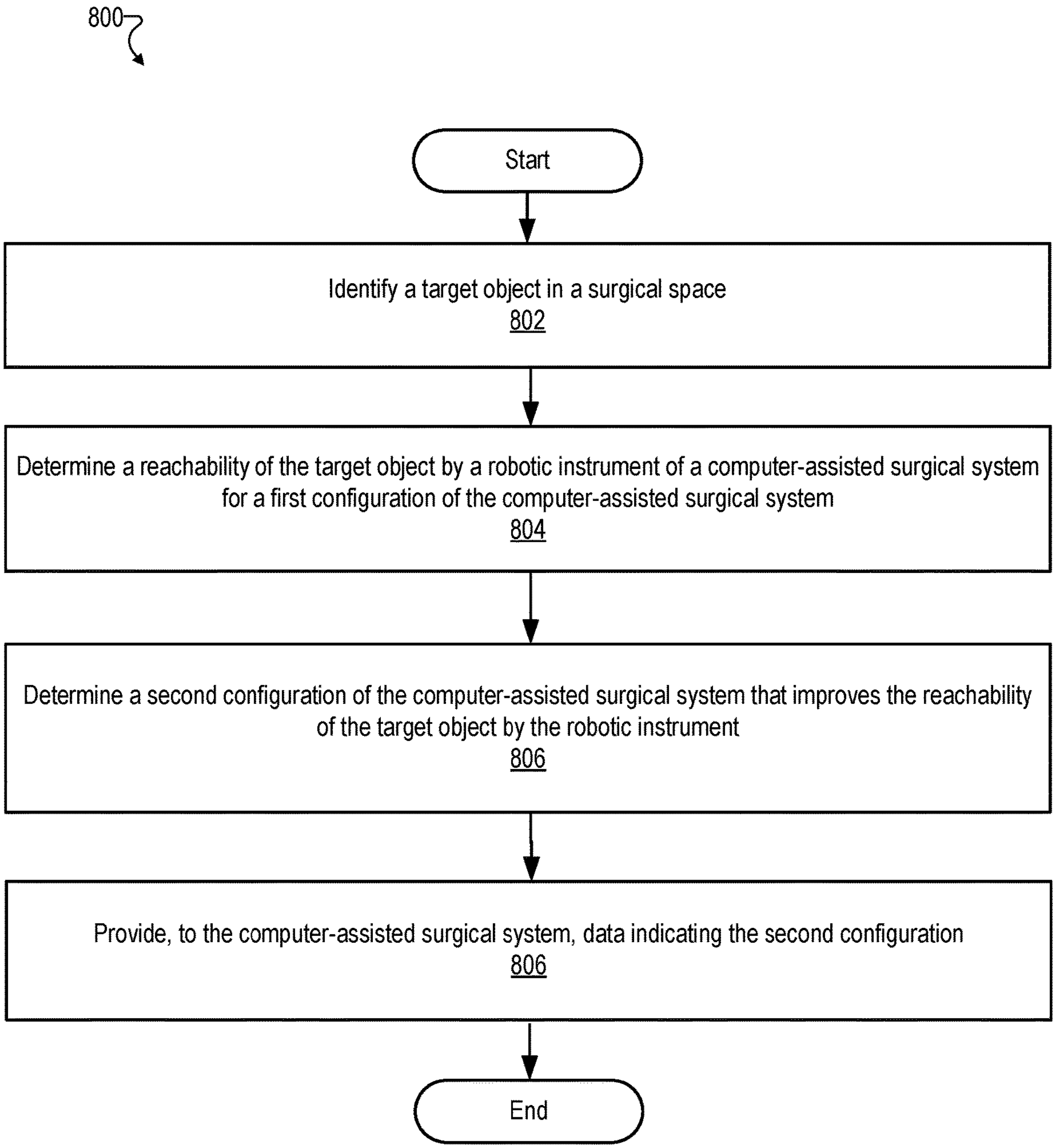
FIG. 8 illustrates an exemplary method for optimizing configurations of a computer-assisted surgical system for reachability of target objects according to principles described herein.

FIG. 8 illustrates an exemplary method 800 for optimizing configurations of a computer-assisted surgical system for reachability of target objects. While FIG. 8 illustrates exemplary operations according to one embodiment, other embodiments may omit, add to, reorder, combine, and/or modify any of the operations shown in FIG. 8. One or more of the operations shown in in FIG. 8 may be performed by a configuration optimization system such as system 100, any components included therein, and/or any implementation thereof.

In operation 802, a configuration optimization system may identify a target object in a surgical space. Operation 802 may be performed in any of the ways described herein.

In operation 804, the configuration optimization system may determine a reachability of the target object by a robotic instrument of a computer-assisted surgical system for a first configuration of the computer-assisted surgical system. Operation 804 may be performed in any of the ways described herein.

In operation 806, the configuration optimization system may determine (e.g., based on the reachability) a second configuration of the computer-assisted surgical system that improves the reachability of the target object by the robotic instrument. Operation 806 may be performed in any of the ways described herein.

In operation 808, the configuration optimization system may provide, to the computer-assisted surgical system, data indicating the second configuration. Operation 808 may be performed in any of the ways described herein.

Figure 9:
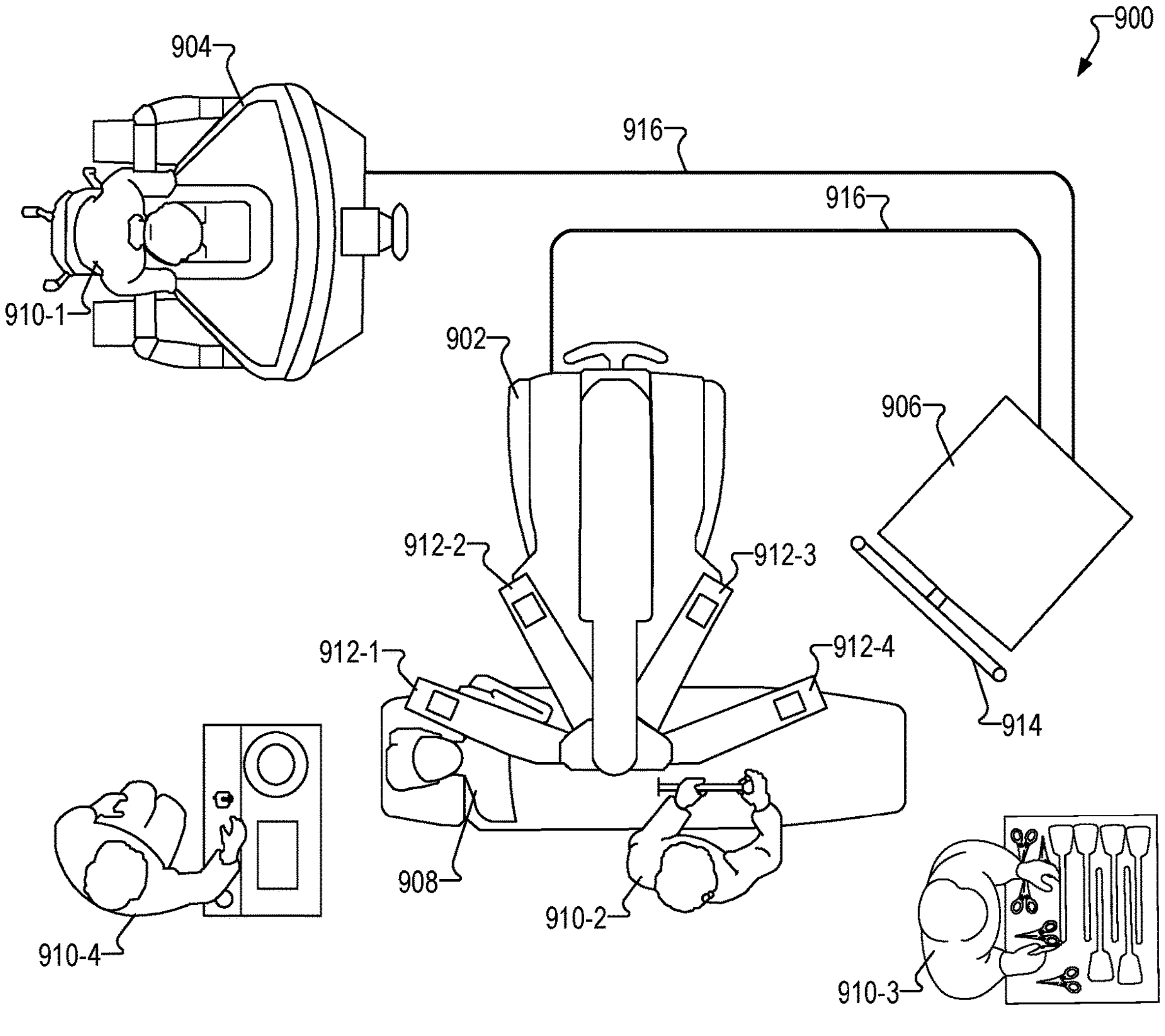
FIG. 9 illustrates an exemplary computer-assisted surgical system according to principles described herein.

FIG. 9 shows an exemplary computer-assisted surgical system 900 ("surgical system 900"). System 100 may be implemented by surgical system 900, connected to surgical system 900, and/or otherwise used in conjunction with surgical system 900.

As shown, surgical system 900 may include a manipulating system 902, a user control system 904, and an auxiliary system 906 communicatively coupled one to another. Surgical system 900 may be utilized by a surgical team to perform a computer-assisted surgical procedure on a patient 908. As shown, the surgical team may include a surgeon 910-1, an assistant 910-2, a nurse 910-3, and an anesthesiologist 910-4, all of whom may be collectively referred to as "surgical team members 910." Additional or alternative surgical team members may be present during a surgical session as may serve a particular implementation.

While FIG. 9 illustrates an ongoing minimally invasive surgical procedure, it will be understood that surgical system 900 may similarly be used to perform open surgical procedures or other types of surgical procedures that may similarly benefit from the accuracy and convenience of surgical system 900. Additionally, it will be understood that the surgical session throughout which surgical system 900 may be employed may not only include an operative phase of a surgical procedure, as is illustrated in FIG. 9, but may also include preoperative, postoperative, and/or other suitable phases of the surgical procedure.

As shown in FIG. 9, manipulating system 902 may include a plurality of manipulator arms 912 (e.g., manipulator arms 912-1 through 912-4) to which a plurality of surgical instruments may be coupled. Each surgical instrument may be implemented by any suitable therapeutic instrument (e.g., a tool having tissue-interaction functions), medical tool, imaging device (e.g., an endoscope), diagnostic instrument, or the like that may be used for a computer-assisted surgical procedure on patient 908 (e.g., by being at least partially inserted into patient 908 and manipulated to perform a computer-assisted surgical procedure on patient 908). In some examples, one or more of the surgical instruments may include force-sensing and/or other sensing capabilities. While manipulating system 902 is depicted and described herein as including four manipulator arms 912, it will be recognized that manipulating system 902 may include only a single manipulator arm 912 or any other number of manipulator arms as may serve a particular implementation.

Manipulator arms 912 and/or surgical instruments attached to manipulator arms 912 may include one or more displacement transducers, orientational sensors, and/or positional sensors used to generate raw (i.e., uncorrected) kinematics information. One or more components of surgical system 900 may be configured to use the kinematics information to track (e.g., determine positions of) and/or control the surgical instruments.

User control system 904 may be configured to facilitate control by surgeon 910-1 of manipulator arms 912 and surgical instruments attached to manipulator arms 912. For example, surgeon 910-1 may interact with user control system 904 to remotely move or manipulate manipulator arms 912 and the surgical instruments. To this end, user control system 904 may provide surgeon 910-1 with imagery (e.g., high-definition 3D imagery) of a surgical area associated with patient 908 as captured by an imaging system (e.g., any of the medical imaging systems described herein). In certain examples, user control system 904 may include a stereo viewer having two displays where stereoscopic images of a surgical area associated with patient 908 and generated by a stereoscopic imaging system may be viewed by surgeon 910-1. Surgeon 910-1 may utilize the imagery to perform one or more procedures with one or more surgical instruments attached to manipulator arms 912.

To facilitate control of surgical instruments, user control system 904 may include a set of master controls. These master controls may be manipulated by surgeon 910-1 to control movement of surgical instruments (e.g., by utilizing robotic and/or teleoperation technology). The master controls may be configured to detect a wide variety of hand, wrist, and finger movements by surgeon 910-1. In this manner, surgeon 910-1 may intuitively perform a procedure using one or more surgical instruments.

Auxiliary system 906 may include one or more computing devices configured to perform primary processing operations of surgical system 900. In such configurations, the one or more computing devices included in auxiliary system 906 may control and/or coordinate operations performed by various other components (e.g., manipulating system 902 and user control system 904) of surgical system 900. For example, a computing device included in user control system 904 may transmit instructions to manipulating system 902 by way of the one or more computing devices included in auxiliary system 906. As another example, auxiliary system 906 may receive, from manipulating system 902, and process image data representative of imagery captured by an imaging device attached to one of manipulator arms 912.

In some examples, auxiliary system 906 may be configured to present visual content to surgical team members 910 who may not have access to the images provided to surgeon 910-1 at user control system 904. To this end, auxiliary system 906 may include a display monitor 914 configured to display one or more user interfaces, such as images (e.g., 2D images, 3D images) of the surgical area, information associated with patient 908 and/or the surgical procedure, and/or any other visual content as may serve a particular implementation. For example, display monitor 914 may display images of the surgical area together with additional content (e.g., graphical content, contextual information, etc.) concurrently displayed with the images. In some embodiments, display monitor 914 is implemented by a touchscreen display with which surgical team members 910 may interact (e.g., by way of touch gestures) to provide user input to surgical system 900.

Manipulating system 902, user control system 904, and auxiliary system 906 may be communicatively coupled one to another in any suitable manner. For example, as shown in FIG. 9, manipulating system 902, user control system 904, and auxiliary system 906 may be communicatively coupled by way of control lines 916, which may represent any wired or wireless communication link as may serve a particular implementation. To this end, manipulating system 902, user control system 904, and auxiliary system 906 may each include one or more wired or wireless communication interfaces, such as one or more local area network interfaces, W-Fi network interfaces, cellular interfaces, etc.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 10:
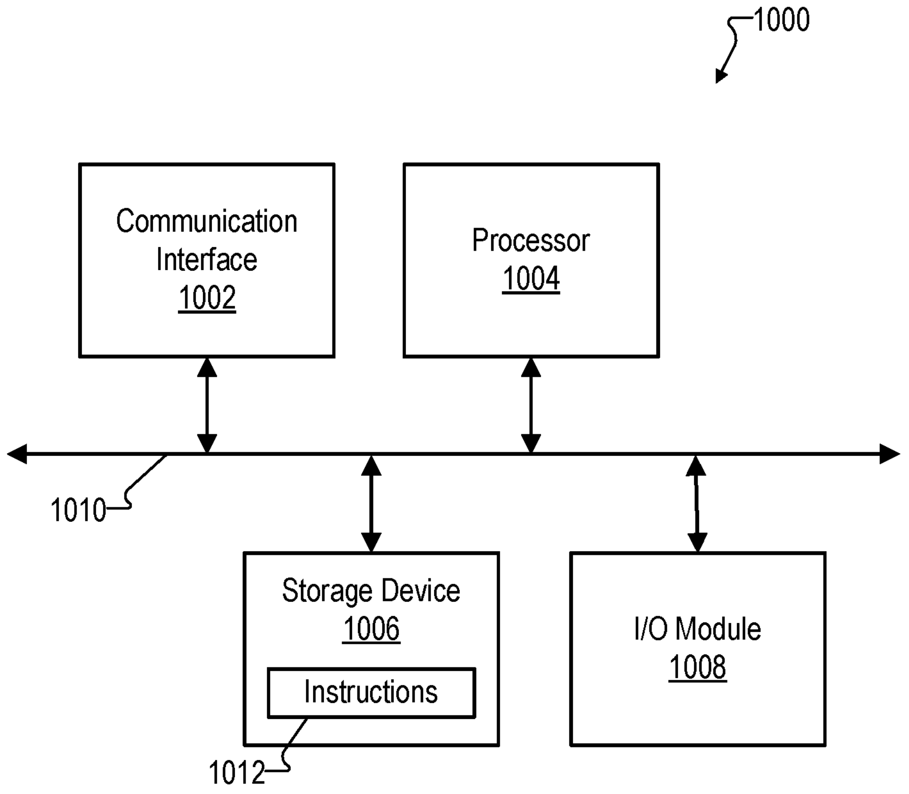
FIG. 10 illustrates an exemplary computing device according to principles described herein.

FIG. 10 illustrates an exemplary computing device 1000 that may be specifically configured to perform one or more of the processes described herein. Any of the systems, units, computing devices, and/or other components described herein may be implemented by computing device 1000.

As shown in FIG. 10, computing device 1000 may include a communication interface 1002, a processor 1004, a storage device 1006, and an input/output ("I/O") module 1008 communicatively connected one to another via a communication infrastructure 1010. While an exemplary computing device 1000 is shown in FIG. 10, the components illustrated in FIG. 10 are not intended to be limiting. Additional or alternative components may be used in other embodiments. Components of computing device 1000 shown in FIG. 10 will now be described in additional detail.

Communication interface 1002 may be configured to communicate with one or more computing devices. Examples of communication interface 1002 include, without limitation, a wired network interface (such as a network interface card), a wireless network interface (such as a wireless network interface card), a modem, an audio/video connection, and any other suitable interface.

Processor 1004 generally represents any type or form of processing unit capable of processing data and/or interpreting, executing, and/or directing execution of one or more of the instructions, processes, and/or operations described herein. Processor 1004 may perform operations by executing computer-executable instructions 1012 (e.g., an application, software, code, and/or other executable data instance) stored in storage device 1006.

Storage device 1006 may include one or more data storage media, devices, or configurations and may employ any type, form, and combination of data storage media and/or device. For example, storage device 1006 may include, but is not limited to, any combination of the non-volatile media and/or volatile media described herein. Electronic data, including data described herein, may be temporarily and/or permanently stored in storage device 1006. For example, data representative of computer-executable instructions 1012 configured to direct processor 1004 to perform any of the operations described herein may be stored within storage device 1006. In some examples, data may be arranged in one or more databases residing within storage device 1006.

I/O module 1008 may include one or more I/O modules configured to receive user input and provide user output. I/O module 1008 may include any hardware, firmware, software, or combination thereof supportive of input and output capabilities. For example, I/O module 1008 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1008 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1008 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1000. For example, one or more applications 1012 residing within storage device 1006 may be configured to direct an implementation of processor 1004 to perform one or more operations or functions associated with processing facility 104 of system 100. Likewise, storage facility 102 of system 100 may be implemented by or within an implementation of storage device 1006.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:

a memory storing instructions;

a processor communicatively coupled to the memory and configured to execute the instructions to:

determine a reachability of a target object by a robotic instrument of a computer-assisted surgical system for a first configuration of the computer-assisted surgical system, the first configuration comprising:

a first master control pose of a set of master controls of the computer-assisted surgical system, the set of master controls configured to control the robotic instrument via a manipulator arm of the computer-assisted surgical system coupled to the robotic instrument, a first robotic instrument pose of the robotic instrument of the computer-assisted surgical system, and a first viewpoint provided by an imaging device of the computer-assisted surgical system, wherein the determining of the reachability of the target object by the robotic instrument includes:

determining, based on the first master control pose, a master control workspace defining an area in which the set of master controls is configured to move, determining a user workspace defining an area in which a user of the set of master controls is able to maneuver the set of master controls, determining a subspace that includes an overlap of the master control workspace and the user workspace, and determining whether a movement of the set of master controls from the first master control pose that corresponds to a movement of the robotic instrument from the first robotic instrument pose to the target object is contained within the subspace;

determine a second configuration of the computer-assisted surgical system that improves the reachability of the target object by the robotic instrument compared to the first configuration, the second configuration comprising a second master control pose that is different from the first master control pose and that improves the reachability of the target object by the robotic instrument controlled by the set of master controls and such that a movement of the set of master controls from the second master control pose that corresponds to the movement of the robotic instrument from the first robotic instrument pose to the target object is contained within the subspace; and facilitate implementation of the second configuration, including directing a decoupling of the master controls from controlling the robotic instrument and, while decoupled, an adjustment of the master controls from the first master control pose to the second master control pose.

2. The system of claim 1, wherein the second configuration includes a second robotic instrument pose of the robotic instrument of the computer-assisted surgical system, the second robotic instrument pose different from the first robotic instrument pose.

3. The system of claim 1, wherein the second configuration includes a second viewpoint provided by the imaging device of the computer-assisted surgical system, the second viewpoint different from the first viewpoint.

4. The system of claim 1, wherein:

the determining of the second configuration includes determining a second viewpoint provided by the imaging device of the computer-assisted surgical system such that the movement of the master controls from the first master control pose that corresponds to the movement of the robotic instrument from the first robotic instrument pose to the target object is contained within the subspace.

5. The system of claim 1, wherein:

the determining of the second configuration includes determining a second viewpoint provided by the imaging device of the computer-assisted surgical system resulting in the second master control pose of the set of master controls such that a movement of the master controls from the second master control pose that corresponds to the movement of the robotic instrument from the first robotic instrument pose to the target object is contained within the subspace.

6. The system of claim 1, wherein:

the determining of the reachability of the target object by the robotic instrument further includes:

determining a first master control workspace defining an area in which the set of master controls is configured to move from the first master control pose, determining a first user workspace defining an area in which a user of the set of master controls is able to maneuver the set of master controls from the first master control pose, determining a first subspace that includes an overlap of the first master control workspace and the first user workspace, and determining that a movement of the set of master controls from the first master control pose that corresponds to a movement of the robotic instrument from the first robotic instrument pose to the target object is not contained within the first subspace; and the determining of the second configuration includes:

determining a second master control pose of the set of master controls resulting in a second master control workspace defining an area in which the set of master controls is configured to move from the second master control pose and a second user workspace defining an area in which the user is able to maneuver the set of master controls from the second master control pose, and optimizing for one of:

the second master control workspace, the second user workspace, or a second subspace that includes an overlap of the second master control workspace and the second user workspace, such that a specific dynamic property is maximized for a movement of the set of master controls from the second master control pose that corresponds to the movement of the robotic instrument from the first robotic instrument pose to the target object.

7. The system of claim 6, wherein:

the second configuration further includes a second viewpoint provided by the imaging device of the computer-assisted surgical system, and the second master control pose is determined by a change between the first viewpoint and the second viewpoint that results in a corresponding change between the first master control pose and the second master control pose.

8. The system of claim 6, wherein the dynamic property includes at least one of an economy of motion, a center of gravity, a number of reachable points, and a size of a workspace.

9. The system of claim 1, wherein the facilitating implementation of the second configuration further includes providing a suggestion to change to the second configuration.

10. A method comprising:

determining, by a processor, a reachability of a target object by a robotic instrument of a computer-assisted surgical system for a first configuration of the computer-assisted surgical system, the first configuration comprising:

a first master control pose of a set of master controls of the computer-assisted surgical system, the set of master controls configured to control the robotic instrument via a manipulator arm of the computer-assisted surgical system coupled to the robotic instrument, a first robotic instrument pose of the robotic instrument of the computer-assisted surgical system, and a first viewpoint provided by an imaging device of the computer-assisted surgical system, wherein the determining of the reachability of the target object by the robotic instrument includes:

determining, based on the first master control pose, a master control workspace defining an area in which the set of master controls is configured to move, determining a user workspace defining an area in which a user of the set of master controls is able to maneuver the set of master controls, determining a subspace that includes an overlap of the master control workspace and the user workspace, and determining whether a movement of the set of master controls from the first master control pose that corresponds to a movement of the robotic instrument from the first robotic instrument pose to the target object is contained within the subspace;

determining a second configuration of the computer-assisted surgical system that improves the reachability of the target object by the robotic instrument compared to the first configuration, the second configuration comprising a second master control pose that is different from the first master control pose and that improves the reachability of the target object by the robotic instrument controlled by the set of master controls and such that a movement of the set of master controls from the second master control pose that corresponds to the movement of the robotic instrument from the first robotic instrument pose to the target object is contained within the subspace; and facilitating implementation of the second configuration, including directing a decoupling of the master controls from controlling the robotic instrument and, while decoupled, an adjustment of the master controls from the first master control pose to the second master control pose.

11. The method of claim 10, wherein the second configuration includes a second robotic instrument pose of the robotic instrument of the computer-assisted surgical system, the second robotic instrument pose different from the first robotic instrument pose.

12. The method of claim 10, wherein the second configuration includes a second viewpoint provided by the imaging device of the computer-assisted surgical system, the second viewpoint different from the first viewpoint.

13. A non-transitory computer-readable medium storing instructions that, when executed by a processor, cause the processor to:

determine a reachability of a target object in a surgical space by a robotic instrument of a computer-assisted surgical system for a first configuration of the computer-assisted surgical system, the first configuration comprising:

a first master control pose of a set of master controls of the computer-assisted surgical system, the set of master controls configured to control the robotic instrument via a manipulator arm of the computer-assisted surgical system coupled to the robotic instrument, a first robotic instrument pose of the robotic instrument of the computer-assisted surgical system, and a first viewpoint provided by an imaging device of the computer-assisted surgical system, wherein the determining of the reachability of the target object by the robotic instrument includes:

determining, based on the first master control pose, a master control workspace defining an area in which the set of master controls is configured to move, determining a user workspace defining an area in which a user of the set of master controls is able to maneuver the set of master controls, determining a subspace that includes an overlap of the master control workspace and the user workspace, and determining whether a movement of the set of master controls from the first master control pose that corresponds to a movement of the robotic instrument from the first robotic instrument pose to the target object is contained within the subspace;

determine a second configuration of the computer-assisted surgical system that improves the reachability of the target object by the robotic instrument compared to the first configuration, the second configuration comprising a second master control pose that is different from the first master control pose and that improves the reachability of the target object by the robotic instrument controlled by the set of master controls and such that a movement of the set of master controls from the second master control pose that corresponds to the movement of the robotic instrument from the first robotic instrument pose to the target object is contained within the subspace; and facilitate implementation of the second configuration, including directing a decoupling of the master controls from controlling the robotic instrument and, while decoupled, an adjustment of the master controls from the first master control pose to the second master control pose.

* * * * *